US005617859A

United States Patent [19]
Souza et al.

[11] Patent Number: 5,617,859
[45] Date of Patent: Apr. 8, 1997

[54] APPARATUS AND METHODS FOR MAGNETIC RESONANCE (MR) IMAGING OF CAVITIES USING FLUIDS POLARIZED AT LOW TEMPERATURES

[75] Inventors: Steven P. Souza, Williamstown, Mass.; Charles L. Dumoulin, Ballston Lake, N.Y.; Robert D. Darrow, Scotia, N.Y.; Harvey E. Cline, Schenectady, N.Y.

[73] Assignee: General Electric Company, Schenectady, N.Y.

[21] Appl. No.: 537,574

[22] Filed: Oct. 2, 1995

[51] Int. Cl.$^6$ ............................................. A61B 5/055
[52] U.S. Cl. ................................ 128/653.2; 128/653.4; 128/653.3; 324/309
[58] Field of Search ........................... 128/653.1, 653.2, 128/653.3, 653.4; 324/307, 309

[56] References Cited

U.S. PATENT DOCUMENTS 5,357,959  10/1994  Fishman .
5,479,925   1/1996  Dumoulin et al. .

OTHER PUBLICATIONS

"MRI Using Hyperpolarized Gas" By G.A. Johnson, R.D. Black, G. Cates, G. Cofer, R. Gunther, W. Happer, L.W. Hedlund, H. Middleton & J. Swartz, Proceedings of the Society of Magnetic Resonance and the European Society for Magnetic Resonance in Medicine and Biology, Nice, France, Aug. 19–25, 1995, vol. 1 pp. 392.

*Primary Examiner*—Marvin M. Lateef
*Assistant Examiner*—Shawna J. Shaw
*Attorney, Agent, or Firm*—Lawrence P. Zale; Marvin Snyder

[57] ABSTRACT

A magnetic resonance (MR) active invasive device system employs a small, high-field polarizing magnet, and a large magnetic resonance (MR) imaging magnet for the purpose of generating MR images of selected body cavities. A subject is positioned in a large low-field MR imaging magnet. A substance, intended to be used as a contrast agent is first cooled, and then passed through the small high-field polarizing magnet where it becomes highly polarized. The substance is then heated to physiologic temperatures, vaporized, and introduced into the subject through a transfer conduit as a vapor. Radiofrequency (RF) pulses and magnetic field gradients are then applied to the patient as in conventional MR imaging. Since the vapor is highly polarized, it can be imaged even though it has a much lower density than the surrounding tissue.

7 Claims, 3 Drawing Sheets

APPARATUS AND METHODS FOR MAGNETIC RESONANCE (MR) IMAGING OF CAVITIES USING FLUIDS POLARIZED AT LOW TEMPERATURES

CROSS REFERENCES TO RELATED APPLICATIONS

This application is related to U.S. patent applications "MAGNETIC RESONANCE (MR) ANGIOGRAPHY IN A LOW-FIELD IMAGING MAGNET" by C. Dumoulin, R. Darrow, Ser. No. 08/264,283, filed Jun. 23, 1994; "MAGNETIC RESONANCE (MR) ANGIOGRAPHY USING A TOROIDAL POLARIZING MAGNET AND A LOW-FIELD IMAGING MAGNET" by C. Dumoulin and R. Darrow, Ser. No. 08/534,998, filed Sep. 27, 1995; "MAGNETIC RESONANCE (MR) ANGIOGRAPHY USING AN INTEGRATED POLARIZING AND IMAGING MAGNET" by C. Dumoulin and S. Souza, Ser. No. 08/537,573, filed Oct. 2, 1995, now U.S. Pat. No. 5,603,320 issued Feb. 18, 1997, "APPARATUS AND METHODS FOR MAGNETIC RESONANCE (MR) ANGIOGRAPHY USING HYDROGEN POLARIZED AT LOW TEMPERATURES" by S. Souza and C. Dumoulin, Ser. No. 08/537,571, filed Oct. 2, 1995; "APPARATUS AND METHODS FOR MAGNETIC RESONANCE (MR) ANGIOGRAPHY USING FLUIDS POLARIZED AT LOW TEMPERATURES" by C. Dumoulin, S. Souza and R. Darrow, Ser. No. 08/537,572, filed Oct. 2, 1995; and "MAGNETIC RESONANCE (MR) PERFUSION IMAGING IN A LOW-FIELD IMAGING MAGNET" by C. Dumoulin and S. Souza, Ser. No. 08/537,575, filed Oct. 2, 1995; all assigned to the present assignee, and all incorporated by reference.

BACKGROUND OF THE INVENTION

1. Field of the Invention

The present invention relates to medical imaging of body cavities, and more particularly concerns the use of magnetic resonance to obtain such images.

2. Description of Related Art

Imaging of cavities is closely related to the imaging of the interior volumes of blood vessels.

Angiography, or the imaging of vascular structures, is very useful in diagnostic and therapeutic medical procedures. MR angiography is performed with a variety of methods, all of which rely on one of two basic phenomena. The first phenomenon arises from changes in longitudinal spin magnetization as blood moves from one region of the patient to another. Methods that make use of this phenomenon have become known as "in-flow" or "time-of-flight" methods. A commonly used time-of-flight method is three-dimensional time-of-flight angiography. With this method, a region of interest is imaged with a relatively short repetition time, TR, and a relatively strong excitation radio-frequency (RF) pulse. This causes the MR spins within the field-of-view to become saturated and give weak MR response signals. Blood flowing into the field-of-view, however, enters in a fully relaxed state. Consequently, this blood gives a relatively strong MR response signal, until it too becomes saturated. Because of the nature of blood vessel detection with time-of-flight methods, the stationary tissue surrounding the vessel cannot be completely suppressed. In addition, slowly moving blood, and blood that has been in the imaged volume for too long, becomes saturated and is poorly imaged.

A second type of MR angiography is based on the induction of phase shifts in transverse spin magnetization. These phase shifts are directly proportional to velocity and are induced by flow-encoding magnetic field gradient pulses. Phase-sensitive MR angiography methods exploit these phase shifts to create images in which the pixel intensity is a function of blood velocity. While phase-sensitive MR angiography can easily detect slow flow in complicated vessel geometries, it will also detect any moving tissue within the field-of-view. Consequently, phase-sensitive MR angiograms of anatomy such as the heart have artifacts arising from the moving muscle and from the moving pools of blood.

Recently, new MR methods for imaging cavities in the body have been disclosed in "MRI Using Hyperpolarized Gas" by A. Johnson et al. p. 392, *Proc. of the Soc. Magn. Resn.*, Third Scientific Meeting and Exhibition, Nice, France Aug. 19–25, 1995 Vol. 1. These methods employ a noble gas such as xenon or helium which is polarized by interactions with optically pumped rubidium. This method requires a laser and related apparatus. Also, the method requires that the rubidium be removed with a high degree of efficiency since rubidium is toxic. Noble gases are known to produce anesthetic effects, and can, in sufficient concentration, be considered to be toxic.

Currently, there is a need for a system for obtaining high quality MR imaging of a selected cavity within the body without the risks of exposure to ionizing radiation and X-ray opaque contrast injections and without use of materials hazardous to humans and animals.

SUMMARY OF THE INVENTION

A substance in the liquid state is passed through a polarizing means before it is vaporized and introduced into a selected cavity of a patient. The polarization means includes a high field magnet in which the substance is placed. The substance is made to reside in the polarizing magnetic field for a period longer than several times the longitudinal relaxation time, T1, of the substance. In an alternative embodiment, additional polarization may be obtained by lowering the temperature of the substance to form a frozen solid. After the substance has become highly polarized, it is removed from the polarizing magnet and rapidly heated to physiologic temperatures and then vaporized. This polarized vapor is then introduced into the patient. MR images of the polarized vapor are created with an MR system which is comprised of radio-frequency and magnetic field gradient coils and a static field imaging magnet. Since the strength of the detected MR signal is determined by the degree of polarization within the introduced vapor, and not the strength of the imaging magnet, resistive or permanent imaging magnets may be used instead of a higher field superconducting magnet.

OBJECTS OF THE INVENTION

It is an object of the present invention to provide a system for non-invasively imaging selected cavities of a subject using magnetic resonance.

It is another object of the present invention to provide a polarization means which can create highly polarized states in selected samples.

It is another object of the present invention to provide a means for the delivery of a highly polarized sample into a patient.

It is yet another object of the present invention to provide MR imaging of cavities without introducing toxic materials into the body.

BRIEF DESCRIPTION OF THE DRAWINGS

The features of the invention believed to be novel are set forth with particularity in the appended claims. The invention itself, however, both as to organization and method of operation, together with further objects and advantages thereof, may be best understood by reference to the following description taken in conjunction with the accompanying drawing in which:

DETAILED DESCRIPTION OF THE INVENTION

Figure 1:
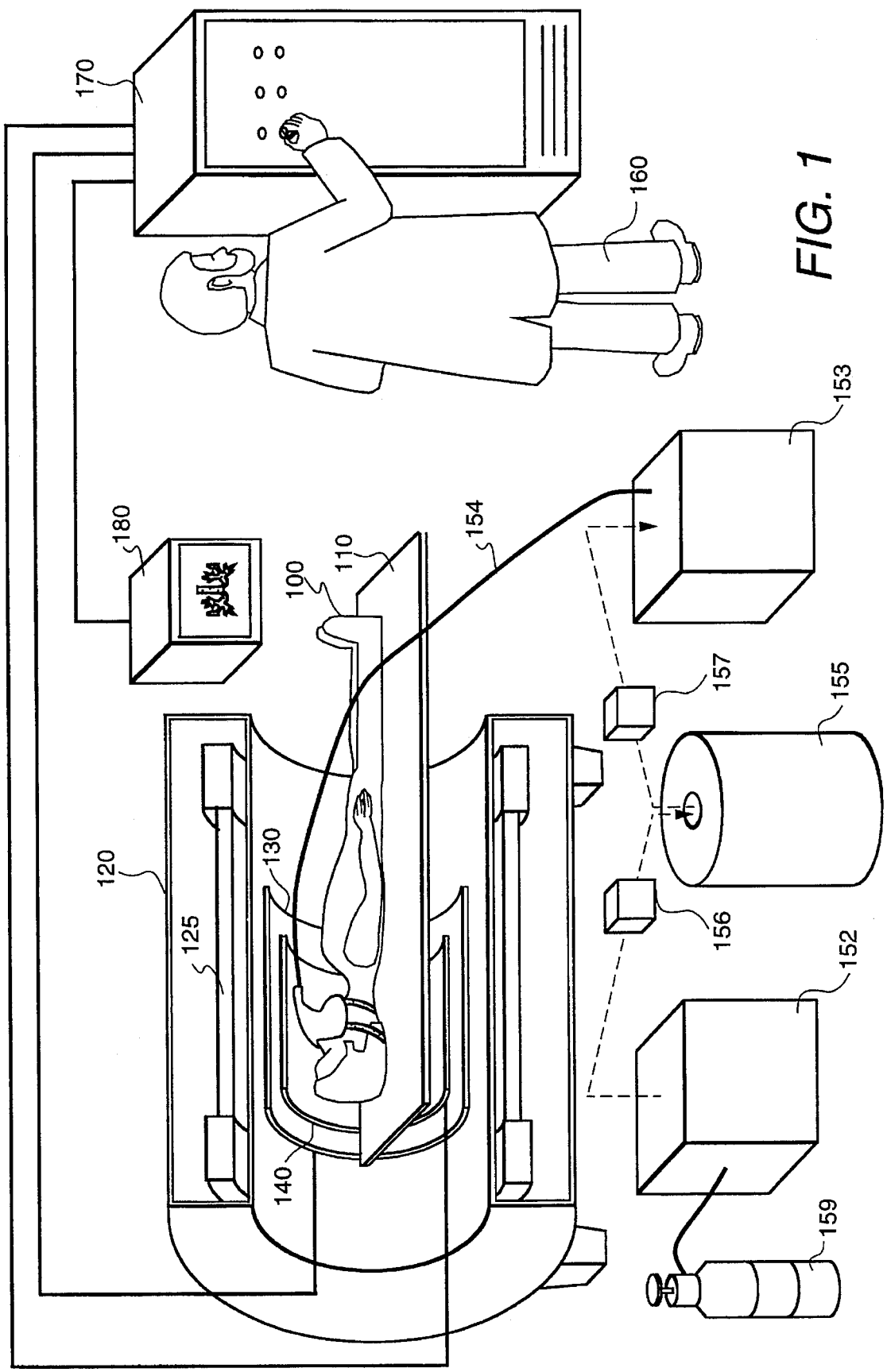
FIG. 1 is a perspective view of a first embodiment of the present invention in operation in which an image of the air space within the lungs is being obtained from a subject.

In FIG. 1, a subject 100 is placed on a support table 110 and positioned in a homogeneous magnetic field generated by a magnet 125 encased in a magnet housing 120. In this embodiment, magnet 125 and magnet housing 120 have cylindrical symmetry and are shown sectioned in half to reveal the position of subject 100. A region of interest of subject 100 is located in the approximate center of the bore of magnet 125. Subject 100 is surrounded by a set of cylindrical magnetic field gradient coils 130 which create magnetic field gradients when energized of predetermined strength at predetermined times according to predetermined MR pulse sequences, described later. Gradient coils 130 are capable of generating pulsed magnetic field gradients in three mutually orthogonal directions. At least one radio-frequency (RF) coil 140 (only one is shown in FIG. 1) also surrounds the region of interest of subject 100. In FIG. 1, RF coil 140 has a cylindrical shape with a diameter sufficient to encompass the entire subject. Other geometries, such as smaller cylinders specifically designed for imaging the head or an extremity, can be used in alternative embodiments. Non-cylindrical RF coils, such as surface coils, may also be used. RF coil 140 radiates radio-frequency energy into subject 100 at predetermined times and with sufficient power at a predetermined frequency so as to nutate a population of nuclear magnetic spins, hereinafter referred to as 'spins', of subject 100 in a fashion well known to those skilled in the art. RF coil 140 can also act as a receiver, detecting the MR response signals which are stimulated by nutation, if desired.

The nutation of the spins causes the spins to resonate at the Larmor frequency. The Larmor frequency for each spin is directly proportional to the strength of the magnetic field experienced by the spin. This field strength is the sum of the static magnetic field generated by magnet 125 and the local field generated by magnetic field gradient coil 130.

A selected fluid or gas suitable for introduction as a vapor into subject 100 is first passed to through a cryogenic pellet forming means 152 which converts the selected fluid into frozen pellets. These pellets are then transferred to a polarizing magnet 155 where they become highly polarized. The pellets can be transferred to polarizing magnet 155 by a first mechanical transfer means 156 or manually in an insulated container.

Polarizing magnet 155 is a superconducting magnet operating with relatively poor homogeneity if desired, but as high a field as practical. Designs in which the field strength reaches 15 Tesla or more are possible. If desired, the magnet can be substantially shielded to prevent stray magnetic fields from disturbing the surrounding environment. This shielding can be accomplished with an active cancellation coil surrounding the internal main coil. Since polarizing magnet 155 is not required to be highly homogeneous, and because of its small size, the magnet should be considerably less expensive than existing MR imaging magnets.

Once the pellets become highly polarized, they are removed from polarizing magnet 155 and put into a physiologic conditioner 153 where the pellets are rapidly melted and brought to approximately body temperature to give a highly polarized fluid. Transfer of the polarized pellets can be performed with a second mechanical transfer means 157, or manually.

The highly polarized fluid is converted to a vapor and then passed through a transfer conduit 154 into a cavity in subject 100 where it is imaged using conventional MR imaging methods. FIG. 1 shows the subject breathing in the vapor to image nasal sinuses, and other portions of the respiratory tract. However, the vapor may be introduced into the auditory passages, colon, or portions of the intestinal tract. The vapor may also be artificially injected by syringe aspiration to other parts of subject 100 for imaging of the desired cavities.

The vapor which is introduced into the subject 100 through transfer conduit 154 should have the highest amount of polarization possible once it reaches the cavity to be imaged. Consequently, the polarizing field of polarizing magnet 155 should be high as possible without regard to the homogeneity of the field produced. Also, the frozen fluid will have to be left in the polarizing field for a period of time greater than five times the T1 of the fluid to reach full magnetization. Once the frozen fluid is removed from polarizing magnet 155 it will begin to lose polarization with a time constant of T1. Since the T1 of the frozen fluid is likely to be long, it may be possible to move the frozen fluid relatively slowly, or even place it in storage for a selected time. As the fluid approaches room temperature, however, the T1 will shorten and transfer of the polarized fluid to physiological conditioner 153 and then through transfer conduit 154 to subject 100 should be as rapid as possible.

In the current invention additional polarization is obtained by lowering the temperature of the pellets. The amount of additional polarization (and hence MR signal) can be derived from the Boltzmann equation:

$$n_e/n_0 = \exp\{-(E_e-E_0)/kT\} \quad (1)$$

where $n_e$ is the number of spins in the excited state, $n_0$ is the number of spins in the ground state, $E_e$ is the energy of the excited state, $E_0$ is the energy of the ground state, k is Boltzmann's constant and T is the temperature of the spins. It is useful to note that as the static magnetic field is increased, the energy of the excited state, $E_e$, increases. This results in a decrease in the ratio of the number of spins in the excited state, $n_e$, with respect to the number of spins in the ground state, $n_0$. Since the polarization of an ensemble of spins is directly proportional to the difference in the number of spins in the excited and ground states, stronger static magnetic fields give greater polarization and consequently, are often desirable. It is also useful to note in equation (1)

that as the temperature, T, is lowered, the polarization of the spins increases. Consequently, an ensemble of spins which are polarized at low temperature attain a stronger degree of polarization.

Since it is the difference in the number of spins in the ground and excited states which determine the strength of the MR signal, S, it is useful to reformulate equation (1) such that:

$$S=C(n_0-n_e) \quad (2)$$

and $$S=C\{n_0\{1-\exp\{-(E_e-E_0)/kT\}\}\} \quad (3)$$

where C is a constant of proportionality.

Equation (3) can be used to calculate the change in signal intensity expected as the temperature, T, of the spins is changed. For example, if the temperature of the spins is lowered from room temperature to four degrees Kelvin, equation (3) predicts a 66.5 fold increase in signal.

Figure 2:
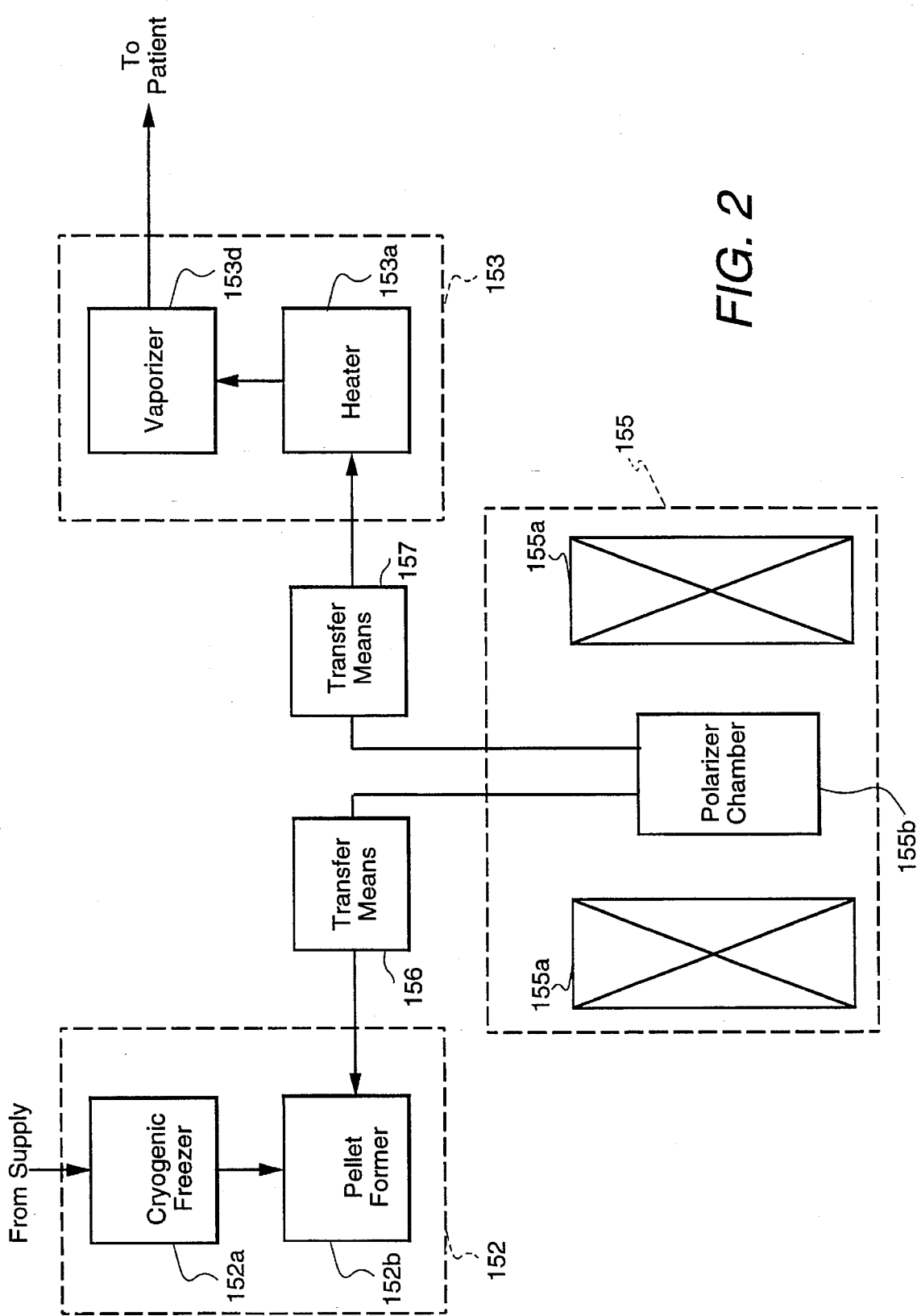
FIG. 2 is a schematic view of one embodiment of the present invention in which a liquid material is frozen, polarized and then prepared for introduction into the subject.

FIG. 2 is a schematic diagram illustrating the components needed to produce highly polarized vapor suitable for introduction into subject 100. Non-polarized fluid from a supply (159 of FIG. 1) is first introduced into cryogenic pellet forming means 152. Cryogenic pellet forming means 152 is comprised of a freezer portion 152a and a pellet former 152b which rolls or presses the frozen fluid into a pellet. The net effect of cryogenic pellet forming means 152 is to convert the non-polarized fluid into a non-polarized solid at low temperature.

The non-polarized solid is then transferred to a polarizing magnet 155 where it is polarized. The solid approaches full polarization in an exponential fashion and polarization in excess of 99% of the maximum value can be achieved by allowing the solid to be in polarizing magnet 155 longer than five times the T1 of the solid. It should be noted that the T1 of the solid is likely to be relatively long at low temperatures.

After the solid has reached the desired level of polarization, the solid can be removed from polarizing magnet 155 and placed into a physiologic conditioner 153. Physiologic conditioner 153 includes a heater 153a which rapidly raises the temperature of the highly-polarized solid to convert it to a liquid at a temperature which would not injure subject 100. The highly-polarized liquid is converted to a vapor by a vaporizer 153b again of a temperature which would not injure subject 100.

The polarized vapor is then introduced into cavities such as the lungs of subject 100 through a transfer conduit 154, the polarized vapor is then imaged providing an indication of air cavities such as the lungs of subject 100. Other methods of introducing vapor in cavities of subject 100 may be envisioned for different orifices thereby providing images of the associated body cavities.

The current invention discloses the formation of pellets, but other embodiments in which a rod is extruded and passed through polarizing magnet 155 on its way to physiologic conditioner 153 are possible. Other embodiments in which cryogenic pellet forming means 152, polarizing magnet 155 and physiologic conditioner 153 are combined into a single apparatus are also possible.

It should be noted that the alternate polarizing method described in patent applications: "APPARATUS AND METHODS FOR MAGNETIC RESONANCE (MR) ANGIOGRAPHY USING HYDROGEN POLARIZED AT LOW TEMPERATURES" by S. Souza and C. Dumoulin, Ser. No. 08/537,571, filed Oct. 2, 1995; in which high degrees of polarization are achieved can be advantageously used with the present invention.

Once the nuclear spins leave polarizing magnet 155 they will begin to lose polarization with a half-life equal to their T1. Consequently, it is desirable to deliver the spins to the patient as quickly as possible. This can be done by minimizing the length of transfer conduit 154 and maximizing the flow velocity.

The fluid used to make the vapor used with the present invention should have a T1 chosen to be as long as possible to maximize the amount of polarization delivered into the cavities of the patient. Possible choices of fluid are:
  1) water
  2) physiological saline solution;
  3) halogenated molecules such as fluorocarbons; and
  4) a noble gas such as helium or xenon.

The imaging system will have many of the same elements as a conventional MR imaging system. A static magnetic field from a main imaging magnet is shown as 125 in FIGS. 1, 3. A small high-field polarization magnet 155 polarizes the fluid.

Figure 3:
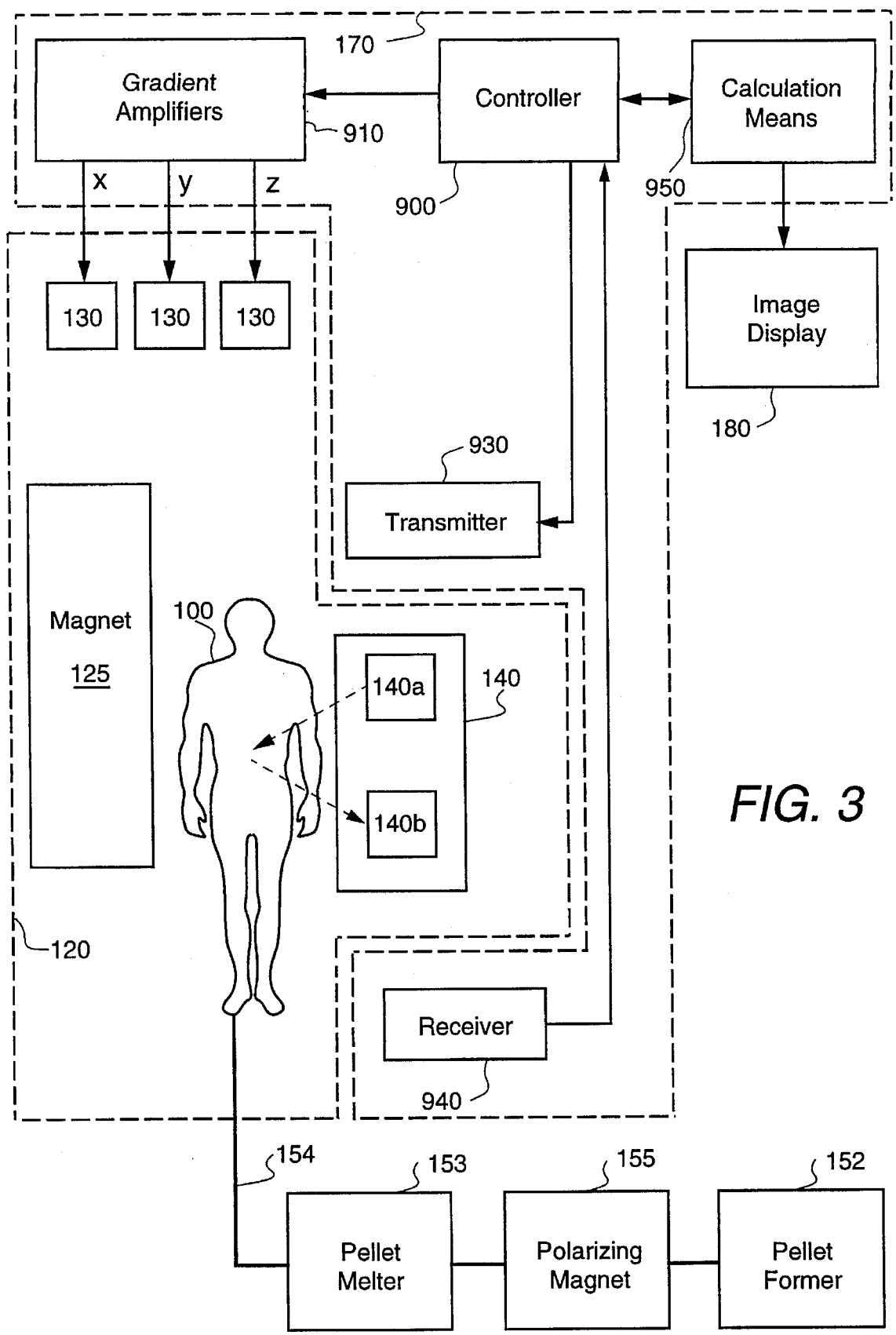
FIG. 3 is a simplified block diagram of a cavity selective MR imaging system suitable for MR cavity imaging according to the present invention.

RF transmitter 930 and RF receiver 940 of the MR system shown in FIG. 3 would be modified to be compatible with the low-field magnet to resonate at a Larmor frequency corresponding to the strength of magnet 125 and the gyromagnetic ratio of the selected substance being imaged.

RF transmitter 930, and RF coil 140 of the present invention perform the same functions as an RF subsystem of a conventional MR imaging device. Because the Larmor frequency is very low, however, RF coil designs having resonant frequencies comparable to the Larmor frequency will be required. At these lower frequencies, very little RF transmit power will be required, being a further advantage of the present invention.

A controller 900 provides control signals to magnetic field gradient amplifiers 910. These amplifiers drive magnetic field gradient coils 130 situated within the magnet enclosure 120. Gradient coils 130 are capable of generating magnetic field gradients in three mutually orthogonal directions.

Controller 900 generates signals which are supplied to RF transmitter 930 to generate RF pulses at one or more predetermined frequencies and with suitable power to nutate selected spins within RF coil 140 situated within the bore of magnet 125. Separate RF transmit 140a and receive 140b coils may be employed instead of a single RF transmit and receive coil 140.

MR response signals are sensed by RF coil 140 connected to receiver 940. Since the polarized fluid has passed through polarizing magnet 155, it acquires a significantly larger longitudinal magnetization, $M_L$, than 'spins' which are only subjected to low-field magnet 125. Consequently, when nutated by the RF pulses, 'spins' which have passed through polarizing magnet 155 exhibit larger transverse magnetization, $M_L$, and consequently produce a much larger MR response signal. Receiver 940 processes the MR response signals by amplifying, demodulating, filtering and digitizing. Controller 900 also collects the signals from receiver 940 and propagates them to a calculation means 950 where they are processed. Calculation means 950 applies a Fourier transformation to the signals received from controller 900 to create an MR image. The image created by calculation means 950 is displayed on an image display means 180.

The contrast ratio of signals from subject 100 can be estimated for an embodiment of the present invention in which a 1.0 Tesla imaging magnet is used with a 10.0 Tesla polarizing magnet and a cryogenic pellet former operating at 4 degrees Kelvin. The 'spins' in subject 100 which did not pass through polarizing magnet 155 experience a 1.0 T magnetic field. Spins that pass through the 10 T polarizing magnet, however, will have a polarization which is 10 times stronger. Spins polarized at 4 degrees Kelvin have an additional factor of 66.5 in polarization. Therefore, the MR signal difference, or contrast, between polarized and non-polarized 'spins' would be a factor of 665.

The signal intensity of a gas in an MR image is approximately 1000 times less than that found in a liquid due to lower spin concentrations. Consequently, in the embodiment of the current invention described above, a polarized gas would have a signal intensity comparable to that of the surrounding tissue.

In another embodiment of the current invention additional image contrast is obtained by acquiring cavity images with and without the introduction of highly polarized vapor. A difference image is then computed causing signals from the tissue surrounding the cavity of interest to be suppressed while highlighting the signals present in the cavity of interest.

The MR system outlined in FIG. 3 may also be used for the generation of conventional MR images in a manner well known to those skilled in the art. Received MR response signals are detected with either the same RF coil used by the transmitter or a surface coil independent of the coil driven by the transmitter.

While several presently preferred embodiments of the novel MR cavity imaging system have been described in detail herein, many modifications and variations will now become apparent to those skilled in the art. It is, therefore, to be understood that the appended claims are intended to cover all such modifications and variations as fall within the true spirit of the invention.

What is claimed is:

1. A magnetic resonance (MR) imaging system for obtaining cavity-selective MR images from a subject comprising:
   a) an imaging magnet for applying a substantially uniform magnetic field over said subject;
   b) a cryogenic pellet-forming means for freezing a portion of a selected substance to form pellets;
   c) a high-field polarizing magnet for polarizing the pellets;
   d) a physiologic conditioner means for converting the polarized pellets into a polarized contrast vapor suitable for introduction into said subject;
   e) a transfer conduit for routing the polarized contrast vapor from the physiologic conditioner means to said subject;
   f) an RF transmitter means for transmitting RF energy into said subject of a selected duration, amplitude and frequency to cause nutation of the contrast vapor and other selected tissues within said subject;
   g) a gradient means for varying the amplitude of the magnetic field in at least one spatial dimension over time;
   h) an RF receive coil for detecting a set of MR response signals from the contrast vapor and other selected tissues within said subject;
   i) a receiver means coupled to the RF receive coil for receiving the detected MR response signals;
   j) a calculation means for calculating an image from the detected MR response signals;
   k) a controller means connected to the RF transmitter means, the receiver means, the calculation means and the gradient means, for activating the RF transmitter means, the receiver means, the calculation means and the gradient means each according to a predetermined MR pulse sequence; and
   l) a display means connected to the calculation means for displaying the calculated image to an operator.

2. A method of obtaining magnetic resonance (MR) images from a cavity of a subject comprising:
   a) applying a substantially homogeneous magnetic field over said subject;
   b) cooling a contrast substance to form a solid;
   c) polarizing the solid by passing it through a high-field polarizing magnet;
   d) vaporizing the polarized solid to obtain a polarized contrast vapor;
   e) routing the polarized contrast vapor into a selected cavity of said subject;
   f) transmitting RF energy into said subject of a selected duration, amplitude and frequency to cause nutation of the contrast vapor and other selected tissues within said subject;
   g) varying the amplitude of the magnetic field in at least one spatial dimension over time;
   h) detecting a set of MR response signals from the polarized contrast vapor and other selected tissues within said subject;
   i) receiving the detected MR response signals;
   j) calculating an image from the detected MR response signals; and
   k) displaying the calculated image to an operator.

3. The method of obtaining magnetic resonance (MR) images from a cavity of a subject of claim 2 wherein the polarized contrast vapor is routed into lungs of the subject to provide MR images of the inside of the lung cavities.

4. The method of obtaining magnetic resonance (MR) images from a cavity of a subject of claim 2 wherein the polarized contrast vapor is routed into the subject's colon to provide MR images of the inside of the colon.

5. The method of obtaining magnetic resonance (MR) images from a cavity of a subject of claim 2 wherein the polarized contrast vapor is routed into the subject's nasal sinus to provide MR images of the inside of the nasal sinus.

6. The method of obtaining magnetic resonance (MR) images from a cavity of a subject of claim 2 wherein the polarized contrast vapor is routed into the subject's intestinal tract to provide MR images of the inside of the intestinal tract.

7. The method of obtaining magnetic resonance (MR) images from a cavity of a subject of claim 2 wherein the polarized contrast vapor is routed into the subject's auditory passages to provide MR images of the inside of the auditory passages.

* * * * *